(12) United States Patent
Njardarson et al.

(10) Patent No.: US 10,370,385 B2
(45) Date of Patent: Aug. 6, 2019

(54) TRICYCLIC MOSQUITOCIDES AND METHODS OF MAKING AND USING THEREOF

(71) Applicant: The Arizona Board of Regents on Behalf of the University of Arizona, Tucson, AZ (US)

(72) Inventors: Jon Njardarson, Tucson, AZ (US); Jun Isoe, Tuscon, AZ (US); Roger Miesfeld, Tucson, AZ (US)

(73) Assignee: Arizona Board of Regents on Behalf of the University of Arizona, Tucson, AZ (US)

( * ) Notice: Subject to any disclaimer, the term of this patent is extended or adjusted under 35 U.S.C. 154(b) by 0 days.

(21) Appl. No.: 15/325,320

(22) PCT Filed: Jul. 10, 2015

(86) PCT No.: PCT/US2015/040034
§ 371 (c)(1),
(2) Date: Jan. 10, 2017

(87) PCT Pub. No.: WO2016/007913
PCT Pub. Date: Jan. 14, 2016

(65) Prior Publication Data
US 2017/0166580 A1 Jun. 15, 2017

Related U.S. Application Data

(60) Provisional application No. 62/022,771, filed on Jul. 10, 2014.

(51) Int. Cl.
*C07D 495/04* (2006.01)
*A01N 43/90* (2006.01)

(52) U.S. Cl.
CPC ........... *C07D 495/04* (2013.01); *A01N 43/90* (2013.01)

(58) Field of Classification Search
USPC ........................................................ 514/411
See application file for complete search history.

(56) References Cited

U.S. PATENT DOCUMENTS 3,901,897 A 8/1975 Hauck

FOREIGN PATENT DOCUMENTS

WO 98013345 4/1998

OTHER PUBLICATIONS

Li et al. Angew Chem Int Ed (2012), 51(8), p. 1938-1941 (disclosed in IDS and provided by Applicants).*
Li et al. Angew Chem Int Ed (2012), 51 (8), pi 938-1941, supporting material pp. 1-60 at pp. 19-20.*
Yadav et al., J Org Chem (2002), 67, p. 1109-1117.*
Baldwin, et al., "Diastereoselective diels-adler reactions between substituted 1, 3-butadienes and n-[alpha]-methylbenzylmaleimide" Tetrahedron Ltrs., 32(42):5877-80 (1991).
Bradford, et al., "Practical synthesis and reactivity of [3] dendralene" J Organic Chem., 75(2):491-4 (2010).
Datta, et al., "Effect of allylic substituents on the face selectivity of diels-adler reactions of semicyclic dienes" J Am Chem Soc., 112(23):8472-8 (1990).
Grafton, et al., "diastereoselective synthesis of highly substituted polycyclic scaffolds via a one-pot four-step tandem catalytic process" Tetrahedron, 70(40):7133-41 (2014).
Iovinella, et al., "A rationale to design longer lasting mosquito repellents" Parasitol Res, 113(5):1813-20 (Mar. 6, 2014).
Li, et al., "Efficient synthesis of thiopyrans using a sulfur-enabled anionic cascade" Ang Chemie Intl., 51(8):1938-41 (2012).
Mack, et al., "Distinct Biological Effects of Golgicide A Derivatives on Larval and Adult Mosquitos" Bioorg. Med. Chem. Lett., 22: 5177 (2012).
Paluch, et al., "Mosquito repellents: a review of chemical structural diversity and olfaction" Pest Manag Sci., 66(9):925-35 (2010).
Smith, et al., "Synthesis of morphine analogs, Part 2, Substituted pyrrolo[3,4-h]isoquinolines" J Chem Soc, Perkins Trans 1, 11(1):2868-72 (1972).
Ting, et al., "Gold-catalyzed isomerization of unactivated allenes into 1,3-dienes under ambient conditions" Chem Comm., 48(52):6577 (2012).
Villemin, et al., "Polycyclic phosphonic acid derivatives obtained by a [4+2] cycloaddition strategy using phosphonodienes" Tetrahedron, 69(3):1138-47 (2012).
Yadav, et al., "Heteroatom influence on the [pi]-facial selectivity of diels-adler cycloadditions to 1-oxa-4-thia-6-vinylspiro [4.5] dec-6-ene, 3-methoxy-3-methyl-2-vinylcyclohexene, and 3-methoxy-2-vinlcyclohexene+, +" J Organic Chem., 67(4):1109-17 (2002).
International Search Report for corresponding PCT application PCT/US2015/040034 dated Sep. 10, 2015.

\* cited by examiner

*Primary Examiner* — Yong L Chu
(74) *Attorney, Agent, or Firm* — Pabst Patent Group LLP

(57) ABSTRACT

Compounds that inhibit digestion in blood-ingesting pests are described herein. In one embodiment, the compounds described herein block entry of blood into the midgut and thereby inhibit digestion and nutrient processing. In another embodiment, the compounds described herein prevent pathogens contained in the blood meal from entering the midgut where they could cross the epithelial cell layer and infect the mosquito. The compounds can be administered to a population of blood-ingesting pests, such as mosquitos, directly or indirectly in an effective amount to prevent mosquitoes from transmitting diseases such as malaria, dengue fever, West Nile virus and lymphatic filariasis. Preferably, the compounds are lethal to blood-ingesting pests. The compounds can be combined with one or more excipients to prepare compositions.

20 Claims, 1 Drawing Sheet

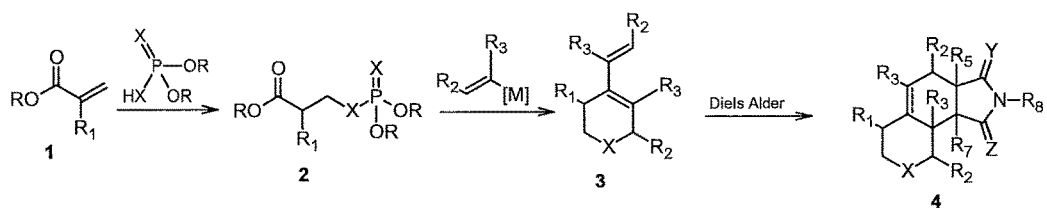

TRICYCLIC MOSQUITOCIDES AND METHODS OF MAKING AND USING THEREOF

CROSS REFERENCE TO RELATED APPLICATIONS

This application is a 371 application of International Application No. PCT/US2015/040034, filed Jul. 10, 2015, which claims priority to and benefit of U.S. Provisional Application No. 62/022,771 filed on Jul. 10, 2014, the disclosures of which are incorporated herein by reference in their entirety.

STATEMENT REGARDING FEDERALLY SPONSORED RESEARCH OR DEVELOPMENT

This invention was made with government support under Grant Nos. R01 AI031951 and R01 AI046541 awarded by NIH. The government has certain rights in the invention.

FIELD OF THE INVENTION

The present invention relates to compounds and compositions for controlling blood-ingesting pests, and methods of making and using thereof. In specific embodiments, the compounds are mosquitocides.

BACKGROUND OF THE INVENTION

Many blood-ingesting pests are known to feed on humans and animals. These pests are vectors for pathogenic microorganisms which threaten human and animal health, including commercially important livestock, pets and other animals. Mosquitoes, a blood-ingesting pest, transmit diseases caused by viruses, and many are vectors for disease-causing nematodes and protozoa, including malaria, filariasis, dengue, yellow fever and encephalitis. The World Health Organization (WHO) estimates that more than 300 million clinical cases each year are attributable to mosquito-borne illnesses. Despite great strides over the last 50 years, mosquito-borne illnesses continue to pose significant risks to the population.

The transmission of mosquito-borne diseases is dependent on a threshold density of competent vector mosquitoes and a reservoir of infected hosts. In the case of Dengue virus, the fastest growing mosquito-borne disease globally in terms of infected humans/yr (~250 million), competent vectors are several species of *Aedes* mosquitoes, most importantly, the species *Aedes aegypti*. Malaria, which is still is a serious threat in many parts of the world, is mainly transmitted by the *Anopheles* mosquitoes, the most important vectors being *Anopheles dirus, Anopheles minimus, Anopheles philippinensis*, and *Anopheles sundaicus*. The spread of mosquito-borne diseases can be restricted by decreasing mosquito populations in areas of high pathogen transmission.

Various pesticides have been employed in efforts to control or eradicate populations of disease-bearing blood-ingesting pests. To date, only four classes of pesticides, which share two modes of action, are approved by the World Health Organization (WHO) for eradicating mosquitoes. One class of pesticide is chlorinated hydrocarbons, for example dichlorodiphenyltrichloroethane (DDT). DDT has been used in attempts to eradicate malaria-bearing mosquitoes throughout the world. Other examples of chlorinated hydrocarbons are benzene hexachloride, lindane, chlorobenzilate, methoxychlor, and the cyclodienes (e.g., aldrin, dieldrin, chlordane, heptachlor, and endrin). The long-term stability of many of these pesticides and their tendency to bioaccumulate render them particularly dangerous to many non-pest organisms.

The pyrethroids, another class of pesticides, include products such as permethrin (Biomist®), resmethrin (Scourge®) and sumithrin (Anvil®). Although pyrethroids are derived from plants, inhalation of these pesticides are known to cause adverse side effects, such as coughing, wheezing, shortness of breath, runny or stuffy nose, chest pain, or difficulty breathing and skin contact may lead to rash, itching, or blisters. The long term effects due to pyrethroid exposure include disruption of the endocrine system in human males; the estrogenizing effects of pyrethroids can cause lowered sperm counts. Long term exposure can also lead to the abnormal growth of breast tissue, development of breasts in males and cancerous breast tissue in both male and females. Pyrethroids also pose neurotoxic effects and are known carcinogens.

Another class of pesticides is the organophosphates, which is perhaps the largest and most versatile class of pesticides. Organophosphates include, for example, parathion, Malathion™, diazinon, naled, methyl parathion, and dichlorvos. Organophosphates are generally much more toxic than the chlorinated hydrocarbons. Their pesticidal effect results from their ability to inhibit the enzyme cholinesterase, an essential enzyme in the functioning of the insect nervous system. However, they also have toxic effects on many animals, including humans.

The carbamates, a relatively new group of pesticides, include such compounds as carbamyl, methomyl, and carbofuran. These compounds are rapidly detoxified and eliminated from animal tissues. Their toxicity is thought to involve a mechanism similar to the mechanism of the organophosphates; consequently, they exhibit similar shortcomings, including animal toxicity.

In addition to the adverse side effects due to insecticide exposure discussed above, blood-ingesting pests can develop resistances to these classes of compounds. A mutation at a single target site can result in mosquito resistance to DDT and pyrethroids or to organophosphates and carbamates. Species of *Anopheles* mosquitoes, for example, have been known to develop resistance to DDT and dieldrin. DDT substitutes, such as Malathion™, propoxur and fenitrothion are available; however, the cost of these substitutes is much greater than the cost of DDT. Mosquitoes can also express multiple insecticide-resistance mechanisms (Perera M D B, et al.; Malar J. 2008; 7:168). For example, in several populations of the major malaria vector in Africa, *Anopheles gambiae* mosquitoes, mutations in the DDT/pyrethroid target site, known as knockdown resistance (kdr) alleles, have been found in conjunction with resistance alleles of the acetylcholinesterase gene (Ace-1R), the target site of organophosphates and carbamates (Yewhalaw, et al.; PLoS ONE. 2011; 6:e16066.).

There is a longstanding need for pesticidal compounds that are pest-specific, that reduce or eliminate direct and/or indirect threats to human health posed by presently available pesticides, that are environmentally compatible, are not toxic to non-pest organisms, and have reduced or no tendency to bioaccumulate.

In mosquitoes, the conversion of protein from a blood meal into yolk proteins and lipids for the developing oocytes is an essential part of the reproductive cycle. Blood feeding by a female *Aedes aegypti* mosquito initiates a series of events in the midgut, the fat body and the ovaries. Female mosquitoes ingest more than their own weight in blood in a short time and then spend the next 36 hours converting the amino acids from the blood proteins into the constituents of their eggs, a process termed vitellogenesis. The process begins in the midgut with the digestions of blood meal proteins and the regulation of digestive enzyme synthesis in the midgut occurs in two phases. The early phase begins immediately after ingestion of the meal and involves activation of translation. The synthesis of early trypsin serves as a model for this phase. The late phase begins 6-8 hours after the meal and involves activation of transcription. The synthesis of late trypsin serves as a model for this phase.

It is believed that this regulatory mechanism is not restricted to mosquitoes considering that the evolutionarily-related sandfly, which is the insect vector for *Leishmania* parasites, has a very similar blood feeding mechanism.

Blood meal feeding in pests creates a unique metabolic challenge as a result of the extremely high protein and iron content of blood.

It is therefore an object of the invention to provide improved compounds to control or eradicate populations of blood feeding pests, such as mosquitoes.

It is a further object of the invention to provide improved compounds that are lethal to blood feeding pests, such as blood-feeding mosquitoes.

It is a further object of the invention to provide improved compounds that prevent or reduce the spread of illnesses by blood-feeding pests.

It is a further object of the invention to provide improved methods for control the reproduction of or eradicate blood feeding pests, such as mosquitoes.

It is a further object of the invention to provide improved methods for preventing or reducing the spread of illnesses by blood feeding pests, such as mosquitoes.

SUMMARY OF THE INVENTION

Compounds that can interfere with blood meal metabolism in a pest, such as a mosquito, and compositions containing such compounds are described herein. These compositions can be used to administer an effective amount of the compound to reduce, prevent the growth or, or even eradicate, a population of pests that feed on human blood and function as disease vectors in an area. Preferably the compounds are safe for use in agricultural areas and do not affect arthropods that do not function as vectors of human pathogens, such as beneficial arthropods, for example pollinators (e.g. bees), and animals.

Methods of making and using these compounds and compositions are also described herein.

The compounds have the formula below:

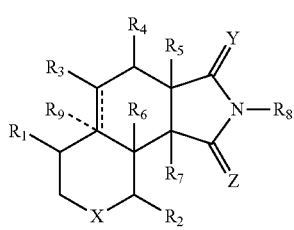

wherein
X is O, S, $CR_{10}R_{11}$, $SiR_{10}R_{11}$, or $NR_{10}$;
Y is O, S, $CR_{10}R_{11}$;
Z is O, S, $CR_{10}R_{11}$;

$R_1$-$R_{11}$ are independently selected from the group consisting of hydrogen, hydroxyl, cyano, nitro, halogen, $NH_2$, SH, $SR_{12}$, $OR_{12}$, $N(R_{12})_2$, $OCON(R_{12})_2$, $C(=O)R_{12}$, $OC(=O)R_{12}$, $C(=O)OR_{12}$, COOH, $COO^-M^+$, $CONH_2$, $CON(R_{12})_2$, $C(=O)H$, substituted or unsubstituted linear, branched, or cyclic alkyl, alkenyl, or alkynyl; substituted or unsubstituted linear, branched, or cyclic heteroalkyl, heteroalkenyl, or heteroalkynyl, substituted or unsubstituted aryl or heteroaryl, $(C(R_{12})_2)_nOH$, $SOR_{12}$, $SOOR_{12}$, $SO_3R_{12}$, $SO_4R_{12}$, $NR_{12}COR_{13}$, phosphoryl, sulfamoyl, and sulfonamido; wherein each occurrence of $R_{12}$ or $R_{13}$ is selected from the group consisting of hydrogen, substituted or unsubstituted linear, branched, or cyclic alkyl, alkenyl, or alkynyl; substituted or unsubstituted linear, branched, or cyclic heteroalkyl, heteroalkenyl, or heteroalkynyl, substituted or unsubstituted aryl or heteroaryl; and the dotted line represents a bond that is either present or absent.

The compounds can be combined with one or more excipients to prepare the compositions. Preferably the excipients are environmentally compatible, more preferably the excipients are not toxic to plants and animals. The compositions can be administered to a population of arthropods, preferably blood ingesting mosquitos, other flies or bugs, or to a region that such pests generally inhabit by any route of administration, such as impregnated bed nets and indoor residual spraying, or any other method for administering insecticides. The compounds and compositions may be useful for inhibiting blood-ingesting pests including, but are not limited to mosquitoes; flies such as deer flies, sand flies, horse flies; lice; and bugs, such as bed bugs and body louse.

In one embodiment, the compounds described herein block entry of blood into the midgut and thereby inhibit digestion and nutrient processing. In another embodiment, the compounds described herein prevent pathogens contained in the blood meal from entering the midgut where they could cross the epithelial cell layer and infect the mosquito. In this embodiment, the compounds prevent mosquitoes from transmitting diseases such as malaria, dengue fever, West Nile virus and lymphatic filariasis.

In the preferred embodiment, the compounds described herein are lethal to blood-ingesting pests that are insect vectors of human pathogens, such as mosquitoes and sandflies.

BRIEF DESCRIPTION OF THE DRAWINGS

FIG. 1 shows a general synthetic scheme of the tricyclic mosquitocides. The compounds are synthesized by reacting sulfur containing dienes with a nitrogen containing dienophile.

DETAILED DESCRIPTION OF THE INVENTION

I. Definitions

An "effective amount", e.g., of the compounds described herein, refers to an amount of the compound in a composition which, when applied as part of an insecticide treatment brings about a change in the pests or their larvae. For example, the change may be a change in the length of follicles in mosquito ovaries and/or increases the rate of mortality of mosquito larvae, compared to a control.

"Analog" and "Derivative", are used herein interchangeably, and refer to a compound that possesses the same tricyclic core as the parent compound but differs from the parent compound in bond order, in the absence or presence of one or more atoms and/or groups of atoms, and combinations thereof. The derivative can differ from the parent compound, for example, in one or more substituents present on the tricyclic core, which may include one or more atoms, functional groups, or substructures. The derivative can also differ from the parent compound in the bond order between atoms within the tricyclic core. In general, a derivative can be imagined to be formed, at least theoretically, from the parent compound via chemical and/or physical processes.

"Co-administration", as used herein, includes simultaneous and sequential administration.

"Environmentally compatible" as used herein, refers to those compounds, materials, and/or compositions, which are suitable for use in contact with plants and animals, the tissues of human beings and animals without excessive toxicity, irritation, allergic response, or other problems or complications commensurate with a reasonable benefit/risk ratio.

"Prodrug", as used herein, refers to a pharmacological substance (drug) that is administered to a subject in an inactive (or significantly less active) form. Once administered, the prodrug is metabolized in the body (in vivo) into a compound having the desired pharmacological activity. Examples include, but are not limited to, esters (generated from hydroxy and carboxylic acid groups), sulfates and phosphates (generated from hydroxy groups on the drug), amides, imines, and carbonates (generated from amino groups on the drug), and imines, oximes, acetals, enol esters, oxazolidines, and thiazolidines (generated from aldehydes and ketones on the drug).

"Alkyl", as used herein, refers to the radical of saturated or unsaturated aliphatic groups, including straight-chain alkyl, alkenyl, or alkynyl groups, branched-chain alkyl, alkenyl, or alkynyl groups, cycloalkyl, cycloalkenyl, or cycloalkynyl (alicyclic) groups, alkyl substituted cycloalkyl, cycloalkenyl, or cycloalkynyl groups, and cycloalkyl substituted alkyl, alkenyl, or alkynyl groups. Unless otherwise indicated, a straight chain or branched chain alkyl has 30 or fewer carbon atoms in its backbone (e.g., $C_1$-$C_{30}$ for straight chain, $C_3$-$C_{30}$ for branched chain), more preferably 20 or fewer carbon atoms, more preferably 12 or fewer carbon atoms, and most preferably 8 or fewer carbon atoms. In some embodiments, the chain has 1-6 carbons. Likewise, preferred cycloalkyls have from 3-10 carbon atoms in their ring structure, and more preferably have 5, 6 or 7 carbons in the ring structure. The ranges provided above are inclusive of all values between the minimum value and the maximum value.

The term "alkyl" includes "unsubstituted alkyls" and "substituted alkyls", the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, a phosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls.

The alkyl groups may also contain one or more heteroatoms within the carbon backbone. Examples include oxygen, nitrogen, sulfur, and combinations thereof. In certain embodiments, the alkyl group contains between one and four heteroatoms.

"Alkenyl" and "Alkynyl", as used herein, refer to unsaturated aliphatic groups containing one or more double or triple bonds analogous in length (e.g., $C_2$-$C_{30}$) and possible substitution to the alkyl groups described above.

"Aryl", as used herein, refers to 5-, 6- and 7-membered aromatic rings. The ring may be a carbocyclic, heterocyclic, fused carbocyclic, fused heterocyclic, bicarbocyclic, or biheterocyclic ring system, optionally substituted as described above for alkyl. Broadly defined, "Ar", as used herein, includes 5-, 6- and 7-membered single-ring aromatic groups that may include from zero to four heteroatoms. Examples include, but are not limited to, benzene, pyrrole, furan, thiophene, imidazole, oxazole, thiazole, triazole, pyrazole, pyridine, pyrazine, pyridazine and pyrimidine. Those aryl groups having heteroatoms in the ring structure may also be referred to as "heteroaryl", "aryl heterocycles", or "heteroaromatics". The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, and —CN. The term "Ar" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocycles, or both rings are aromatic. Examples of heterocyclic ring include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl.

"Alkylaryl", as used herein, refers to an alkyl group substituted with an aryl group (e.g., an aromatic or hetero aromatic group).

"Heterocycle" or "heterocyclic", as used herein, refers to a cyclic radical attached via a ring carbon or nitrogen of a monocyclic or bicyclic ring containing 3-10 ring atoms, and preferably from 5-6 ring atoms, containing carbon and one to four heteroatoms each selected from non-peroxide oxygen, sulfur, and N(Y) wherein Y is absent or is H, O, ($C_{1-4}$ alkyl, phenyl or benzyl, and optionally containing one or more double or triple bonds, and optionally substituted with one or more substituents. The term "heterocycle" also encompasses substituted and unsubstituted heteroaryl rings. Examples of heterocyclic ring include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl.

"Heteroaryl", as used herein, refers to a monocyclic aromatic ring containing five or six ring atoms containing carbon and 1, 2, 3, or 4 heteroatoms each selected from non-peroxide oxygen, sulfur, and N(Y) where Y is absent or is H, O, ($C_1$-$C_8$) alkyl, phenyl or benzyl. Non-limiting examples of heteroaryl groups include furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide), quinolyl (or its N-oxide) and the like. The term "heteroaryl" can include radicals of an ortho-fused bicyclic heterocycle of about eight to ten ring atoms derived therefrom, particularly a benz-derivative or one derived by fusing a propylene, trimethylene, or tetramethylene diradical thereto. Examples of heteroaryl include, but are not limited to, furyl, imidazolyl, triazolyl, triazinyl, oxazoyl, isoxazoyl, thiazolyl, isothiazoyl, pyraxolyl, pyrrolyl, pyrazinyl, tetrazolyl, pyridyl (or its N-oxide), thientyl, pyrimidinyl (or its N-oxide), indolyl, isoquinolyl (or its N-oxide), quinolyl (or its N-oxide), and the like.

"Halogen", as used herein, refers to fluorine, chlorine, bromine, or iodine.

The term "substituted" as used herein, refers to all permissible substituents of the compounds described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, preferably 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, aminoacid, peptide, and polypeptide groups.

Heteroatoms such as nitrogen may have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc.

The term "pest" as used herein refers to blood—

The term "mosquito" as used herein refers to any species of the ~3,500 species of the insect that is commonly associated with and given the common name "mosquito." Mosquitoes span 41 insect genera, including the non-limiting examples of *Aedes, Culex, Anopheles* (carrier of malaria), *Coquillettidia*, and *Ochlerotatus*.

II. Compounds

Compounds having the formula below and methods of making and using are described herein:

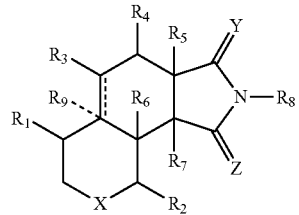

wherein
X is O, S, $CR_{10}R_{11}$, $SiR_{10}R_{11}$, or $NR_{10}$;
Y is O, S, $CR_{10}R_{11}$;
Z is O, S, $CR_{10}R_{11}$;
$R_1$-$R_{11}$ are independently selected from the group consisting of hydrogen, hydroxyl, cyano, nitro, halogen, $NH_2$, SH, $SR_{12}$, $OR_{12}$, $N(R_{12})_2$, $OCON(R_{12})_2$, $C(=O)R_{12}$, $OC(=O)R_{12}$, $C(=O)OR_{12}$, COOH, $COO^-M^+$, $CONH_2$, $CON(R_{12})_2$, $C(=O)H$, substituted or unsubstituted linear, branched, or cyclic alkyl, alkenyl, or alkynyl; substituted or unsubstituted linear, branched, or cyclic heteroalkyl, heteroalkenyl, or heteroalkynyl, substituted or unsubstituted aryl or heteroaryl, $(C(R_{12})_2)_nOH$, $SOR_{12}$, $SOOR_{12}$, $SO_3R_{12}$, $SO_4R_{12}$, $NR_{12}COR_{13}$, phosphoryl, sulfamoyl, and sulfonamido; wherein each occurrence of $R_{12}$ or $R_{13}$ is selected from the group consisting of hydrogen, substituted or unsubstituted linear, branched, or cyclic alkyl, alkenyl, or alkynyl; substituted or unsubstituted linear, branched, or cyclic heteroalkyl, heteroalkenyl, or heteroalkynyl, substituted or unsubstituted aryl or heteroaryl; and the dotted line represents a bond that is either present or absent.

In some embodiments, when $R_1$ is hydrogen, methyl, isopropyl, or ethyl, $R_8$ is not unsubstituted phenyl.

In some embodiments, the compounds have the following stereochemistry:

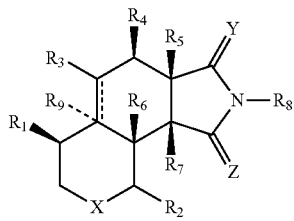

In some embodiments, X is sulfur.
In some embodiments, Y is oxygen.
In some embodiments, Z is oxygen.
In some embodiments, X is sulfur and Y and Z are both oxygen.
In some embodiments, $R_1$ is substituted or unsubstituted alkyl.
In some embodiments, $R_1$ is methyl.
In some embodiments, $R_2$ is hydrogen.
In some embodiments, $R_3$ is hydrogen.
In some embodiments, $R_4$ and $R_5$ are hydrogen.
In some embodiments, $R_6$ is hydrogen.
In some embodiments, $R_7$ is hydrogen.
In some embodiments, $R_8$ is substituted or unsubstituted aryl.
In some embodiments, $R_8$ is substituted or unsubstituted phenyl.
In some embodiments, $R_8$ is unsubstituted phenyl.
In some embodiments, $R_9$ is absent.
In some embodiments, $R_9$ is hydrogen.
In some embodiments, the compound has the fat iula:

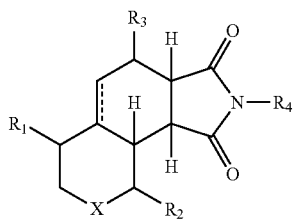

wherein
X is O, S, $CR_5R_6$, $SiR_5R_6$, or $NR_5$;
$R_1$-$R_4$ are independently selected from the group consisting of hydrogen, hydroxyl, cyano, nitro, halogen, $NH_2$, SH, $SR_7$, $OR_5$, $N(R_7)_2$, $OCON(R_7)_2$, $C(=O)R_7$, $OC(=O)R_7$, $C(=O)OR_7$, COOH, $COO^-M^+$, $CONH_2$, $CON(R_7)_2$, $C(=O)H$, substituted or unsubstituted linear, branched, or cyclic alkyl, alkenyl, or alkynyl; substituted or unsubstituted linear, branched, or cyclic heteroalkyl, heteroalkenyl, or heteroalkynyl, substituted or unsubstituted aryl or heteroaryl, $(C(R_7)_2)_nOH$, $SOR_7$, $SOOR_7$, $SO_3R_7$, $SO_4R_7$, $NR_7COR_8$, phosphoryl, sulfamoyl, and sulfonamido; wherein each occurrence of $R_7$ or $R_8$ is selected from the group consisting of hydrogen, substituted or unsubstituted linear, branched, or cyclic alkyl, alkenyl, or alkynyl; substituted or unsubstituted linear, branched, or cyclic heteroalkyl, heteroalkenyl, or heteroalkynyl, substituted or unsubstituted aryl or heteroaryl; and the dotted line represents a bond that is either present or absent.

In another embodiment, the compound has the formula:

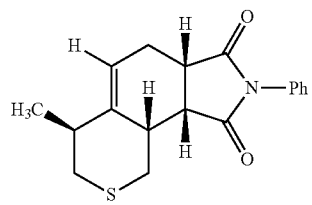

In yet another embodiment, the compound has the formula:

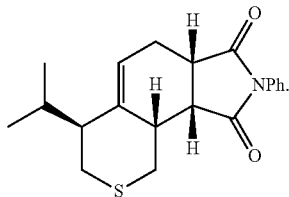

The compounds described herein may have one or more chiral centers, and thus can exist as one or more stereoisomers. Such stereoisomers can exist as a single enantiomer, a mixture of enantiomers, a mixture of diastereomers, or a racemic mixture.

As used herein, the term "stereoisomers" refers to compounds made up of the same atoms having the same bond order but having different three-dimensional arrangements of atoms that are not interchangeable. The three-dimensional structures are called configurations. As used herein, the term "enantiomers" refers to two stereoisomers that are non-superimposable mirror images of one another. As used herein, the term "optical isomer" is equivalent to the term "enantiomer". As used herein the term "diastereomer" refers to two stereoisomers which are not mirror images but also not superimposable. The terms "racemate", "racemic mixture" or "racemic modification" refer to a mixture of equal parts of enantiomers. The term "chiral center" refers to a carbon atom to which four different groups are attached. Choice of the appropriate chiral column, eluent, and conditions necessary to effect separation of the pair of enantiomers is well known to one of ordinary skill in the art using standard techniques (see e.g. Jacques, J. et al., "Enantiomers, Racemates, and Resolutions", John Wiley and Sons, Inc. 1981).

The compounds can also be a pharmaceutically acceptable salt of any of the compounds described above. In some cases, it may be desirable to prepare the salt of a compound described above due to one or more of the salt's advantageous physical properties, such as enhanced stability or a desirable solubility or dissolution profile.

Generally, pharmaceutically acceptable salts can be prepared by reaction of the free acid or base forms of a compound described above with a stoichiometric amount of the appropriate base or acid in water, in an organic solvent, or in a mixture of the two. Generally, non-aqueous media including ether, ethyl acetate, ethanol, isopropanol, or acetonitrile are preferred. Lists of suitable salts are found in Remington's Pharmaceutical Sciences, 20th ed., Lippincott Williams & Wilkins, Baltimore, Md., 2000, p. 704; and "Handbook of Pharmaceutical Salts: Properties, Selection, and Use," P. Heinrich Stahl and Camille G. Wermuth, Eds., Wiley-VCH, Weinheim, 2002.

Suitable pharmaceutically acceptable acid addition salts include those derived from inorganic acids, such as hydrochloric, hydrobromic, hydrofluoric, boric, fluoroboric, phosphoric, metaphosphoric, nitric, carbonic, sulfonic, and sulfuric acids, and organic acids such as acetic, benzenesulfonic, benzoic, citric, ethanesulfonic, fumaric, gluconic, glycolic, isethionic, lactic, lactobionic, maleic, malic, methanesulfonic, trifluoromethanesulfonic, succinic, toluenesulfonic, tartaric, and trifluoroacetic acids.

Suitable organic acids generally include, for example, aliphatic, cycloaliphatic, aromatic, araliphatic, heterocyclic, carboxylic, and sulfonic classes of organic acids. Specific examples of suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, mesylate, stearate, salicylate, p-hydroxybenzoate, phenylacetate, mandelate, embonate (pamoate), methanesulfonate, ethanesulfonate, benzenesulfonate, pantothenate, toluenesulfonate, 2-hydroxyethanesulfonate, sufanilate, cyclohexylaminosulfonate, algenic acid, β-hydroxybutyric acid, galactarate, galacturonate, adipate, alginate, butyrate, camphorate, camphorsulfonate, cyclopentanepropionate, dodecylsulfate, glycoheptanoate, glycerophosphate, heptanoate, hexanoate, nicotinate, 2-naphthalesulfonate, oxalate, palmoate, pectinate, 3-phenylpropionate, picrate, pivalate, thiocyanate, tosylate, and undecanoate.

In some cases, the pharmaceutically acceptable salt may include alkali metal salts, including sodium or potassium salts; alkaline earth metal salts, e.g., calcium or magnesium salts; and salts formed with suitable organic ligands, e.g., quaternary ammonium salts. Base salts can also be formed from bases which form non-toxic salts, including aluminum, arginine, benzathine, choline, diethylamine, diolamine, glycine, lysine, meglumine, olamine, tromethamine and zinc salts.

Organic salts may be made from secondary, tertiary or quaternary amine salts, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups may also be quaternized with agents such as lower alkyl ($C_1$-$C_6$) halides (e.g., methyl, ethyl, propyl, and butyl chlorides, bromides, and iodides), dialkyl sulfates (e.g., dimethyl, diethyl, dibuytl, and diamyl sulfates), long chain halides (e.g., decyl, lauryl, myristyl, and stearyl chlorides, bromides, and iodides), arylalkyl halides (e.g., benzyl and phenethyl bromides), and others.

The compound can also be a prodrug of any of the compounds described above. Prodrugs are compounds that, when metabolized in vivo, undergo conversion to compounds having the desired activity. Prodrugs can be prepared by replacing appropriate functionalities present in the compounds described above with "pro-moieties" as described, for example, in H. Bundgaar, Design of Prodrugs (1985). Examples of prodrugs include ester, ether or amide derivatives of the compounds described above, polyethylene glycol derivatives of the compounds described above, N-acyl amine derivatives, dihydropyridine pyridine derivatives, amino-containing derivatives conjugated to polypeptides, 2-hydroxybenzamide derivatives, carbamate derivatives, N-oxide derivatives that are biologically reduced to the active amines, and N-mannich base derivatives. For further discussion of prodrugs, see, for example, Rautio, J. et al. *Nature Reviews Drug Discovery.* 7:255-270 (2008).

III. Compositions

Compositions are provided containing an effective amount of one or more compound described herein, or a salt or prodrug thereof, in combination with one or more environmentally compatible excipients.

Representative excipients include solvents, diluents, pH modifying agents, preservatives, antioxidants, suspending agents, wetting agents, viscosity modifiers, tonicity agents, stabilizing agents, and combinations thereof. The composition may be prepared as a solution, suspension, dispersion, or an emulsion, such as water-in-oil emulsions, oil-in-water emulsions, and microemulsions thereof.

In some embodiments, the composition contains one or more compounds having the formula

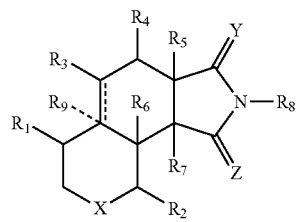

wherein

X is O, S, $CR_{10}R_{11}$, $SiR_{10}R_{11}$, or $NR_{10}$;

Y is O, S, $CR_{10}R_{11}$;

Z is O, S, $CR_{10}R_{11}$;

$R_1$-$R_{11}$ are independently selected from the group consisting of hydrogen, hydroxyl, cyano, nitro, halogen, $NH_2$, SH, $SR_{12}$, $OR_{12}$, $N(R_{12})_2$, $OCON(R_{12})_2$, $C(=O)R_{12}$, $OC(=O)R_{12}$, $C(=O)OR_{12}$, COOH, $COO^-M^+$, $CONH_2$, $CON(R_{12})_2$, $C(=O)H$, substituted or unsubstituted linear, branched, or cyclic alkyl, alkenyl, or alkynyl; substituted or unsubstituted linear, branched, or cyclic heteroalkyl, heteroalkenyl, or heteroalkynyl, substituted or unsubstituted aryl or heteroaryl, $(C(R_{12})_2)_nOH$, $SOR_{12}$, $SOOR_{12}$, $SO_3R_{12}$, $SO_4R_{12}$, $NR_{12}COR_{13}$, phosphoryl, sulfamoyl, and sulfonamido; wherein each occurrence of $R_{12}$ or $R_{13}$ is selected from the group consisting of hydrogen, substituted or unsubstituted linear, branched, or cyclic alkyl, alkenyl, or alkynyl; substituted or unsubstituted linear, branched, or cyclic heteroalkyl, heteroalkenyl, or heteroalkynyl, substituted or unsubstituted aryl or heteroaryl; and the dotted line represents a bond that is either present or absent and one or more pharmaceutically acceptable carriers.

In some other embodiments, the composition contains one or more compounds having the formula

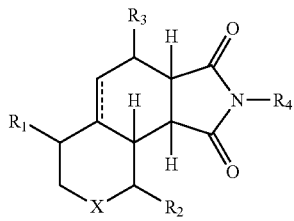

wherein

X is O, S, $CR_5R_6$, $SiR_5R_6$, or $NR_5$;

$R_1$-$R_4$ are independently selected from the group consisting of hydrogen, hydroxyl, cyano, nitro, halogen, $NH_2$, SH, $SR_7$, $OR_5$, $N(R_7)_2$, $OCON(R_7)_2$, $C(=O)R_7$, $OC(=O)R_7$, $C(=O)OR_7$, COOH, $COO^-M^+$, $CONH_2$, $CON(R_7)_2$, $C(=O)H$, substituted or unsubstituted linear, branched, or cyclic alkyl, alkenyl, or alkynyl; substituted or unsubstituted linear, branched, or cyclic heteroalkyl, heteroalkenyl, or heteroalkynyl, substituted or unsubstituted aryl or heteroaryl, $(C(R_7)_2)_nOH$, $SOR_7$, $SOOR_7$, $SO_3R_7$, $SO_4R_7$, $NR_7COR_8$, phosphoryl, sulfamoyl, and sulfonamido; wherein each occurrence of $R_7$ or $R_8$ is selected from the group consisting of hydrogen, substituted or unsubstituted linear, branched, or cyclic alkyl, alkenyl, or alkynyl; substituted or unsubstituted linear, branched, or cyclic heteroalkyl, heteroalkenyl, or heteroalkynyl, substituted or unsubstituted aryl or heteroaryl; and the dotted line represents a bond that is either present or absent.

In yet another embodiment, the composition contains a compound having the formula:

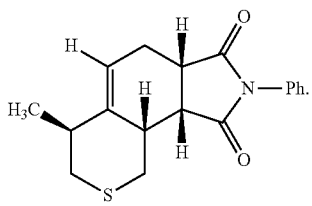

In yet another embodiment, the composition contains a compound having the formula:

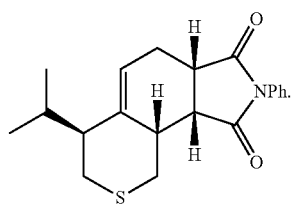

Other (or inert) ingredients may be included in the composition to aid in the application of the compound. Other ingredients include but are not limited to, solvents, carriers, adjuvants, or any other compound, besides the active ingredient. There are many types of other ingredients: solvents are liquids that dissolve the active ingredient, carriers are liquids or solid chemicals that are added to a pesticide product to aid in the delivery of the active ingredient, and adjuvants often help make the pesticide stick to or spread out on the application surface (i.e., leaves). Other adjuvants aid in the mixing of some compositions when they are diluted for application.

The compound may be applied as a solid, such as in the form of pellets or flakes. For example, the compound may be included in a solid pellet that is introduced into a water source.

The compound may be dissolved or dispersed in a continuous phase. The continuous phase typically contains a surfactant wetting agent, e.g. alkyl/aryl polyether alcohols, polyethylene oxide esters (or ethers) of fatty acids, alkyl/aryl sulfonates, alkyl sulfates and the like. The surfactant is preferably present in the amount of about 0.1% up to about 5% vol/vol of the composition. These surface active agents are well known in the art for use in preparing dispersions of insecticides. In the continuous phase of the composition, the surfactants assist in causing the solution droplets to spread out on waxy leaves and penetrate the waxy protective coating on the insects and their eggs.

Suitable surfactants may be anionic, cationic, amphoteric or nonionic surface-active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-β-alanine, sodium N-lauryl-β-iminodipropionate, myristoamphoacetate, lauryl betaine, and lauryl sulfobetaine.

In some embodiments, the compositions can include one or more carriers and/or diluents such as, for example, any solid or liquid carrier or diluent that is commonly used in pesticidal, agricultural, or horticultural compositions. Those skilled in the art will recognize that these components in a composition are typically referred to as "inert ingredients" and are regulated by governmental agencies, such as the U.S. Environmental Protection Agency (EPA). Suitably, any included additional carrier or diluent will not reduce the insecticidal efficacy of the composition, relative to the efficacy of the composition in the absence of the additional component. Carriers and diluents can include, for example, solvents (e.g., water, alcohols, petroleum distillates, acids, and esters); vegetable oil (including but not limited to methylated vegetable oil); and/or plant-based oils as well as ester derivatives thereof (e.g., wintergreen oil, cedarwood oil, rosemary oil, peppermint oil, geraniol, rose oil, palmarosa oil, citronella oil, citrus oils (e.g., lemon, lime, and orange), dillweed oil, corn oil, sesame oil, soybean oil, palm oil, vegetable oil, olive oil, peanut oil, and canola oil). The composition can include varying amounts of other components such as, for example, fatty acids and fatty acid esters of plant oils (e.g., methyl palmitate/oleate/linoleate), and other auxiliary ingredients such as, for example, emulsifiers, dispersants, stabilizers, suspending agents, penetrants, coloring agents/dyes, UV-absorbing agents, and fragrances, as necessary or desired. The compositions may comprise carrier or diluent in an amount of at least about 1%, at least about 2%, or at least about 5% by weight of the composition. The compositions may comprise carrier or diluent in an amount of less than about 30%, less than about 25%, or less than about 20% by weight of the composition. The compositions may comprise carrier or diluent in an amount of about 1% to about 30%, about 2% to about 25%, or about 5% to about 20% by weight of the composition. Components other than mineral oil and coconut oil can be included in the compositions in any amount as long as the composition provides some amount of insecticidal efficacy.

IV. Methods of Making

The compounds disclosed herein and the compositions necessary to perform the disclosed methods can be made using any method known to those of skill in the art for that particular reagent or compound unless otherwise specifically noted. For example, the tricyclic compounds may be synthesized by the method disclosed in Li et al., *Efficient synthesis of thiopyrans using a sulfur-enabled anionic cascade*, Angew. Chem. Int. Ed., 2012, 51:1968-1941.

General Synthetic Scheme

FIG. 1 describes a representative general syntheses of the compounds disclosed herein. The starting ester (1) could be sourced commercially and used without further purification. Reaction of the ester (1) with a phosphate salt, such as thiophosphate yields a phosphate compound (2). Reaction of the phosphate compound (2) with a vinyl Grignard reagent yields a diene pyran product (3). The diene pyran product (3) can then react with a substituted dienophile via Diels-Alder to give one or more of the compounds disclosed herein. Preferably, the dienophile is a substituted 2,5-dihydro pyrrole for example, a maleimide derivative.

In some embodiments, following Diels-Alder reaction, the disclosed compounds may be derived via reduction, oxidation and other functional group interconversions.

V. Methods of Administration

Compositions containing one or more of the compounds described herein can be administered to prevent the spread of mosquito-borne illnesses. Mosquito-borne illnesses include, but are not limited to, mosquito vectored diseases such as protozoan diseases, i.e., malaria, filarial diseases such as dog heartworm, and viruses such as Dengue, encephalitis, West Nile virus, rift valley fever, and yellow fever, as well as severe skin irritation through an allergic reaction to the mosquito's saliva.

The compositions may be delivered directly to mosquitoes using conventional impregnated bed nets, spraying, and/or direct application to a water source. These methods of administration are particularly preferred for use in areas with high transmission rates of mosquito-borne diseases.

In one embodiment, an effective of amount one or more of the compounds described herein is administered to a population of blood-ingesting pests that are vectors for human pathogens, preferably the pests are mosquitos or sandflies, most preferably female mosquitos, to inhibit digestion and nutrient processing in the blood-ingesting pests.

In one embodiment, the method involves administering an effective amount of one or more of the compounds described herein to kill blood-ingesting pests that are vectors for human pathogens, preferably the pests are mosquitos or sandflies, most preferably female mosquitos.

The compounds can be administered to reduce the size of the small and undeveloped follicles (eggs) in the pests.

In some embodiments, the method involves administering an effective amount of one or more of the compounds described herein to blood-ingesting pests that are vectors for human pathogens, preferably the pests are mosquitos or sandflies, most preferably female mosquitos to reduce follicle size to less than 350, 325, 300, 275, 270, 260, 250, 240, or 235 microns. Following administration of the compounds described herein the size of the follicles in the female pests may be reduced by at least 20%, at least 30%, at least 40%, at least 50%, at least 60% compared to the standard follicle size when they are not exposed to the compounds. As shown in the Examples, when the compound was delivered to the female mosquitos, the size of their follicles reduced by greater than 60% compared to the control (DMSO).

Measurements can be carried out using any suitable microscopy technique to evaluate the reduction in follicle size in pests. An exemplary method is described in the Examples.

Pest larval mortality can be evaluated by any standard method. An exemplary method is described in the Examples.

A. Effective Amounts

In some embodiments, the composition is applied in an amount effective to kill at least about 90%, 91%, 92%, 93%, 94%, 95%, 96%, 97%, 98%, or 99% of the contacted pest (e.g. mosquito) population.

In some embodiments, the compositions provided herein have some degree of insecticidal activity, while not necessarily meeting the EPA requirements for an insecticide for certain uses. That is, certain compositions are still considered effective if less than about 95% of the contacted mosquito population is killed, as required by the EPA. In some embodiments, the composition is applied in an amount effective to kill at least about 90%, or less than about 95%, of the contacted pest population, preferably the contacted mosquito population.

In some embodiments, the compositions contain an effective amount of one or more of the compounds to inhibit digestion and nutrient processing in the blood-ingesting pests, particularly to female blood-ingesting mosquitoes.

In some embodiments, the compositions contain an effective amount of one or more of the compounds to reduce follicle size in the female blood-ingesting pests, particularly to female blood-ingesting mosquitoes. Following administration of the compounds described herein the follicles in the female pests may be reduced by at least 20%, at least 30%, at least 40%, at least 50%, at least 60%, preferably the follicle size is reduces between 50% and 70%, compared to the standard follicle size when they are not exposed to the compounds.

In some embodiments, the lethal concentration ($LC_{50}$) against pest larvae, preferably mosquito larvae, most preferably *An. Stephensi* and/or *An. Aegypti* mosquitolarvae, is less than 0.25, 0.20, 0.15, 0.10, or 0.05 mM.

B. Uses

The compounds described herein may be administered to prevent the spread of illnesses caused by blood-ingesting pests. In one embodiment, the compounds block entry of blood into the midgut of blood-ingesting pests, such as mosquitos, and thereby inhibit digestion and nutrient processing. In one embodiment, the compositions inhibit digestion and nutrient processing in blood-ingesting mosquitoes. In another embodiment, the compounds prevent pathogens contained in the blood meal from entering the midgut where they could cross the epithelial cell layer and infect the mosquito. In this embodiment, the compounds prevent mosquitoes from transmitting diseases such as malaria, dengue fever, West Nile virus and lymphatic filariasis. In the preferred embodiment, the compounds described herein are lethal to blood-ingesting pests that are vectors for human pathogens, preferably the pests are mosquitos or sandflies, most preferably female mosquitos In addition to larvicidal properties on *Aedes* and *Anopheles* mosquitoes, the inhibition of midgut blood digestion and presumably pathogen transmission, the compounds in this class are highly selective to the adult *Aedes* female mosquitoes.

Blood-ingesting mosquitoes include, but are not limited to, *Aedes* (*Stegomyia*) spp., including *Aedes aegypti, Aedes albopictus, Aedes polynesiensis* and other members of the *Aedes scutellaris, Anopheles dirus, Anopheles minimus, Anopheles philippinensis*, and *Anopheles sundaicus, Culiseta melanura, Culiseta morsitans, Aedes atlanticus, Culiseta particeps, Aedes atropalpus, Deinocerites cancer, Aedes canadensis, Mansonia titilnans Aedes cantator, Orthopodomyia signifera, Aedes cinereus, Psorophora ciliate, Aedes condolescens, Psorophora columbine, Aedes dorsalis, Psorophora ferox,*

*Aedes dupreei, Psorophora howardii, Aedes epactius, Uranotaenia sapphirina,*

*Aedes fitchii, Aedes fulvus pallens, Aedes grossbecki, Aedes infirmatus, Aedes japonicas, Aedes melanimon, Aedes nigromaculis, Aedes provocans, Aedes sollicitans, Aedes squamiger, Aedes sticticus, Aedes stimulans, Aedes taeniorhynchus, Aedes triseriatus, Aedes trivittatus, Aedes vexans, Anopheles atropos, Anopheles barberi, Anopheles bradleyi/crucians, Anopheles franciscanus, Anopheles freeborni, Anopheles hermsi, Anopheles punctipennis, Anopheles quadrimaculatus, Anopheles walker, Coquillettidia perturbans, Culex apicalis, Culex bahamensis, Culex coronator, Culex erraticus, Culex erythrothorax, Culex nigripalpus, Culex pipiens, Culex quinquefasciatus, Culex restuans, Culex salinarius, Culex stigmatosoma, Culex tarsalis, Culex territans*

*Culex thriambus, Culiseta incidens, Culiseta impatiens,* and *Culiseta inornata.*

In one embodiment, the one or more compounds in the compositions are present in an effective amount to reduce follicle size in blood fed *Ae. Aegypti* mosquitos to less than 350, 325, 300, 275, 270, 260, 250, 240, or 235 microns, as measured by a suitable microscopy technique, such as optical microscopy or SEM.

C. Administration

Suitable methods include contacting a mosquito or population of mosquitos with an effective amount of a composition as described above. Contacting includes contacting an insect directly or indirectly. For example, compositions described herein may be applied to a surface and an insect may subsequently or concurrently contact the surface and the composition. In some embodiments, compositions may be applied to a surface. In some embodiments, compositions may form a coating or film on a surface. In some embodiments, methods include forming a coating or film on a surface.

Surfaces may include, but are not limited to, surfaces of liquid such as bodies of water or other aquatic mosquito breeding sites. Examples of bodies of water and application sites include, without limitation, salt marshes, freshwater aquatic environments, storm water drainage areas, sewers and catch basins, woodland pools, snow pools, roadside ditches, retention ponds, freshwater dredge spoils, tire tracks, rock holes, pot holes, and similar areas subject to holding water; natural and manmade aquatic sites, fish ponds, ornamental ponds, fountains, and other artificial water-holding containers or tanks; flooded crypts, transformer vaults, abandoned swimming pools, construction, and other natural or manmade depressions; stream eddies, creek edges, detention ponds, freshwater swamps and marshes including mixed hardwood swamps, cattail marshes, common reed wetlands, water hyacinth ponds, and similar freshwater areas with emergent vegetation; brackish water swamps, marshes, and intertidal areas; sewage effluent, sewers, sewage lagoons, cesspools, oxidation ponds, septic ditches, and septic tanks; animal waste lagoons, settling ponds, livestock runoff lagoons, and wastewater impoundments associated with fruit and vegetable processing; and similar areas. Other examples include, without limitation, dormant rice fields (for application during the interval between harvest and preparation of the field for the next cropping cycle), standing water within pastures/hay fields, rangeland, orchards, and citrus groves where mosquito breeding occurs.

In some embodiments, the methods described herein can comprise any known route, apparatus, and/or mechanism for the delivery or application of the compositions. In some embodiments, the method comprises applying the compositions via a sprayer. In some embodiments, compositions described herein may be applied at rates of about three gallons to about ten gallons per acre, depending on insect population densities. Traditional pesticide sprayers in the pest control markets are typically operated manually or electrically or are gas-controlled and use maximum pressures ranging from 15 to 500 psi generating flow rates from 1 gpm to 40 gpm.

VI. Kits

Kits containing compositions from greater than about 0.5% to about 80% of the compound by weight of the composition are described herein. In one embodiment, the composition contains the active compound, in the form of the free base or a pharmaceutically acceptable salt.

The compositions may be packaged in any suitable container or source structure affording a desired supply of the composition for its intended purpose. For example, the compositions may be packaged in an aerosol container, as a fogger or spray unit, for fogging, misting or spraying of the pest-control composition to a desired locus of use. The composition alternatively can be packaged in a container equipped with a hand pump dispenser unit or other applicator, administration or dispensing elements. These embodiments are particularly useful for application of the compositions in areas inhabited by blood-ingesting pests that are vectors of human pathogens, such as mosquitos.

EXAMPLES

Example 1: Synthesis of Thiopyrans Using a Sulfur-Enabled Anionic Cascade

General

Commercial reagents were purchased and used without further purification. All glassware was flame dried and reactions were performed under a nitrogen atmosphere, unless otherwise stated. Methylene chloride, tetrahydrofuran, diethyl ether and toluene were dried by passage through a solvent drying system containing cylinders of activated alumina Flash chromatography was done with Silicycle SiliaFlash® F60 silica, and thin layer chromatography (TLC) was performed with EMD 250 µm silica gel 60-F254 plates. $^1$H NMR spectra were acquired using Bruker (400 or 500 MHz) spectrometer with chloroform (7.26 ppm) as internal references. Signals are reported as follows: s (singlet), d (doublet), t (triplet), q (quartet), dd (doublet of doublets), dt (doublet of triplets), br s (broad singlet), m (multiplet). Coupling constants are reported in hertz (Hz). $^{13}$C NMR spectra were acquired on spectrometers operating at 100 or 125 MHz with chloroform (77.23 ppm) as internal reference. Infrared spectra were obtained on an FT-IR spectrometer. *Exemplary synthesis of phosphorodithioate ester*

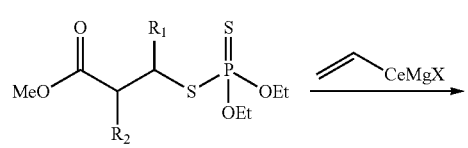

To a solution of ketone (9.2 g, 54.6 mmol) in acetonitrile (80 mL) was added thiophosphate salt (14.2 g, 69.9 mmol). The mixture was then placed in a 70° C. oil bath, and heated for 4 hours. The solution was cooled down to room temperature and filtered over celite. The solvent was removed in vacuo and flash chromatography with silica in (5% EtOAc: 92% hexanes) provided compound A1 (10.44 g, 32.8 mmol, 60%) as a yellow oil.

$^1$H NMR (400 MHz, CDCl$_3$) δ8.07-7.88 (m, 2H), 7.67-7.53 (m, 1H), 7.55-7.41 (m, 2H), 4.36-3.99 (m, 4H), 3.43 (td, J=6.9, 0.7 Hz, 2H), 3.26 (dtd, J=17.9, 6.9, 0.7 Hz, 2H), 1.36 (td, J=7.1, 0.8 Hz, 6H); 13C NMR (100 MHz, CDCl3) δ197.4, 136.3, 133.5, 128.7 (2C), 128.0 (2C), 64.1, 39.3, 27.5, 27.5, 15.9, 15.8; IR (film) 3027.7, 2980.5, 2899.5, 1685.5, 1596.8, 1580.4, 1448.3, 1226.5, 1009.6, 959.4, 749.2, 694.3, 650.9 cm-1; HRMS (ESI+) m/z 341.0417 [calculated mass for C$_{13}$H$_{19}$NaO$_3$S$_2$P (M$^+$Na$^+$) 341.0411].

Synthesis of 3-isopropyl-4-vinyl-3,6-dihydro-2H-thiopyran (9e)

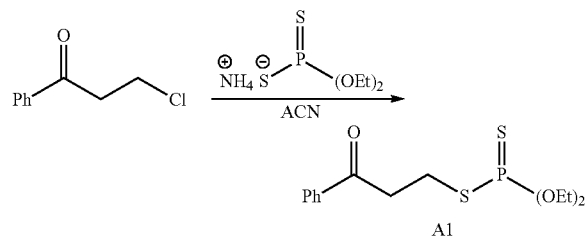

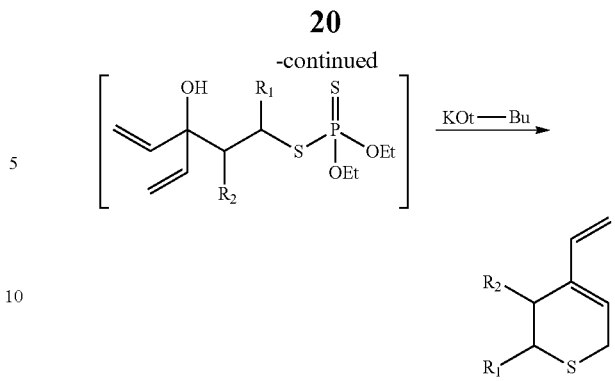

To a flame dried round bottom flask, CeCl$_3$.7H2O powder (6.6 equiv) was added. The flask was placed in a 140° C. oil bath and placed in vacuo for 2 hours. The powder was then cooled down to room temperature, and protected by nitrogen. THF was then added to the flask. The solution was stirred for 1 hour and then further cooled down to -78° C. and stirred for 15 min. Then a 1.0 M vinyl magnesium bromide solution in THF was added (6.6 equiv) and stirred for 1 hour at -78° C. The phosphorodithioate ester (1 equiv) was then added and stirred for 3 hour at -78° C. Then the mixture was warm backed to room temperature and stirred for 48 hours. The mixture was then quenched with 1M HCl and stirred for 1 hour. The aqueous layer was extracted with CH$_2$Cl$_2$ and the combined organic layers were dried with MgSO$_4$, concentrated in vacuo, and dissolved into THF. A solution of potassium tert-butoxide in THF was added dropwise and the mixture was stirred for 5 minutes. After the addition, the colorless and transparent reaction mixture turned into orange and cloudy. The solution was then quenched with 1M HCl and stirred for 1 hour. The aqueous layer was extracted with CH$_2$Cl$_2$ and the combined organic layers were dried with MgSO$_4$, concentrated in vacuo, and isolated by flash chromatography (1% EtOAc-Hexanes elution) on silica gel to yield thiopyran as pale yellow oil.

3-isopropyl-4-vinyl-3,6-dihydro-2H-thiopyran (9e) was isolated by flash column 1% EtOAc-Hexanes elution) on silica gel in 71% yield.) $^1$H NMR (400 MHz, CDCl$_3$) δ6.31 (dd, J=17.4, 10.9 Hz, 1H), 5.99-5.79 (m, 1H), 5.18 (d, J=17.5 Hz, 1H), 5.04-4.91 (m, 1H), 3.34 (dd, J=17.8, 5.0 Hz, 1H), 3.25-3.13 (m, 1H), 2.82-2.66 (m, 2H), 2.48 (dt, J=7.7, 3.8 Hz, 1H), 2.17 (ddq, J=20.5, 13.7, 6.8 Hz, 1H), 0.98 (d, J=6.7 Hz, 3H), 0.93 (d, J=6.9, 3H); 13C NMR (100 MHz, CDCl3) δ141.3, 140.5, 124.8, 111.4, 38.9, 30.0, 27.7, 24.8, 21.6, 20.4; IR (film) 2960.3, 2921.8, 2852.3, 1558.3, 1508.1, 1458.0, 914.1, 746.4 cm-1; HRMS (EI+) m/z 168.0968 [calculated mass for C$_{10}$H$_{16}$S (M$^+$) 168.0973].

Synthesis of 4-isopropyl-8-phenyl-1,3,4,6,6a,9b-hexahydrothiopyrano [3,4]isoindole-7,9(8H9aH)-dione

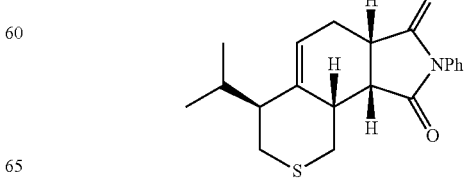

To a dry sealed tube charged with thiopyran (9e; 7.5 mg, 0.044 mmol) solution in toluene (2 mL) was added N-phenylmaleimide 10 (19 mg, 0.089 mmol) and the mixture was stirred at 140° C. for 2 hours. 2 ml H$_2$O was added and the mixture with CH$_2$Cl$_2$ (3×3 mL) and the combined organic layers were dried with MgSO4 and concentrated in vacuo. Flash chromatography (SiO$_2$, 20% EtOAc-hexanes elution) afforded 11 mg (0.033 mmol, 74%) as a pale yellow solid.

$^1$H NMR (400 MHz, CDCl$_3$) δ7.51-7.44 (m, 2H), 7.43-7.37 (m, 1H), 7.27-7.23 (m, 2H), 5.68 (t, J=4.4 Hz, 1H), 3.34-3.21 (m, 2H), 3.13-3.05 (m, 1H), 2.95-2.85 (m, 2H), 2.80-2.71 (m, 1H), 2.64 (ddd, J=18.3, 12.2, 4.7 Hz, 2H), 2.47 (ddd, J=12.9, 8.9, 4.9 Hz, 1H), 2.32 (tt, J=15.4, 6.6 Hz, 1H), 2.22-2.15 (m, 1H), 0.95 (d, J=6.5 Hz, 3H), 0.88 (d, J=6.7 Hz, 3H); 13C NMR (100 MHz, CDCl$_3$) δ178.6, 177.0, 141.4, 131.7, 129.2 (2C), 128.6, 126.3 (2C), 119.3, 50.7, 42.9, 38.0, 36.7, 31.4, 29.8, 26.0, 22.0, 21.5, 20.0; IR (film) 2926.0, 2848.9, 2355.1, 1705.1, 1496.8, 1386.8, 1195.9, 752.2 cm −1; HRMS (EI+) m/z 364.1360 [calculated mass for C$_{20}$H$_{23}$NNaO$_2$S (M$^+$Na$^+$) 364.1347].

Example 2: Delivery of 4-isopropyl-8-phenyl-1,3,4,6,6a,9b-hexahydrothiopyrano [3,4-e]isoindole-7,9(8H,9aH)-dione to Female Mosquitos

*Aedes aegypti* (Rockefeller strain) mosquitoes were reared in standard conditions. Four day old female mosquitoes were microinjected with 200 nL of 5% DMSO (control) or the compound described in Example 1, i.e. 4-isopropyl-8-phenyl-1,3,4,6,6a,9b-hexahydrothiopyrano [3,4-e]isoindole-7,9(8H,9aH)-dione (5.0 mM in 5% DMSO), using Nanoject II (Drummond). The injected mosquitoes were recovered for one day in the environmental chamber and fed on warmed human blood through a membrane feeder. Twenty fully fed mosquitoes from each group were observed under a dissecting microscope for defective phenotypes, including midgut and primary follicle development in the ovaries during the first gonotrophic cycle.

Evaluation of Follicle Size

The mosquitos were reared in environmental chambers. Larvae were then fed with a mixture of tropical flakes, rat chow, liver powder, or cat food pellets. Adult pests were maintained on 10% sucrose. Four-day old mosquitoes were allowed to feed on human blood supplemented with fresh ATP. One hour after blood feeding, the mosquitoes were briefly chilled at 4° C. to immobilize. 200 nl of the compound, 4-isopropyl-8-phenyl-1,3,4,6,6a,9b-hexahydrothiopyrano [3,4-e]isoindole-7,9(8H,9aH)-dione, was diluted in water to a final concentration of 0.7 mM before use. Then the compound was microinjected with a microinjector into fully fed mosquitos. For each experiment, the mosquitoes were also microinjected with 2% DMSO (control). Mosquitos were allowed to feed 10% sucrose, and 48 h post blood meal, ovaries were dissected from the injected mosquitos in 1×PBS under a microscope. Ovaries were teased to separate follicles, and the images were digitally captured for follicle length measurement.

Evaluation of Mosquito Larval Mortality

Two-day-old second instar larvae were transferred to wells in a plate containing 1 ml of larval growth media. The 4-isopropyl-8-phenyl-1,3,4,6,6a,9b-hexahydrothiopyrano [3,4-e]isoindole-7,9(8H,9aH)-dione and DMSO (control) were added directly to the media and swirled. The final concentration of the 4-isopropyl-8-phenyl-1,3,4,6,6a,9b-hexahydrothiopyrano [3,4-e]isoindole-7,9(8H,9aH)-dione in each well was 0.2 mM, the DMSO concentration was 0.2%. The plates were kept in the environmental chamber. Mosquito larvae were examined under a microscope for any sign of mortality 24 hours after exposure. Data obtained from at least three biological replicates were statistically analyzed with the Bonferroni post tests.

Results

Forty percent (40%) of blood-fed mosquitoes injected with the compound 4-isopropyl-8-phenyl-1,3,4,6,6a,9b-hexahydrothiopyrano [3,4-e]isoindole-7,9(8H,9aH)-dione exhibited the defect in the alimentary canal in which the blood meal was misdirected into the ventral diverticulum. This prevented blood meal nutrients from reaching the mosquito midgut and thereby blocked initiation of the gonotrophic cycle, which is required for egg development.

None of the DMSO injected mosquitoes showed the defect of the storage of the blood meal.

Evaluation of Follicle Size

The follicle size in blood-fed mosquitoes injected with the compound 4-isopropyl-8-phenyl-1,3,4,6,6a,9b-hexahydrothiopyrano [3,4-e]isoindole-7,9(8H,9aH)-dione was determined to be 145.6±11.0 μm. In contrast, the follicle size for the control mosquitoes (DMSO) was measured to be 452.8±6.4 μm.

Evaluation of Mosquito Larval Mortality 18 out of 45 mosquito larvae (40%) died following 24 hours of exposure to 4-isopropyl-8-phenyl-1,3,4,6,6a,9b-hexahydrothiopyrano [3,4-e]isoindole-7,9(8H,9aH)-dione (0.2 mM). In contrast all of the larvae in the control survived.

Without being bound by theory, it is believed that the compounds described herein, such as 4-isopropyl-8-phenyl-1,3,4,6,6a,9b-hexahydrothiopyrano [3,4-e]isoindole-7,9(8H,9aH)-dione, interfere with the molecular process required for differential delivery of nectar to the ventral diverticulum and blood meal nutrients to the midgut for nutrient absorption. Mosquito survival and reproductive potential can be significantly reduced when mosquitos do not have the ability to direct nectar and blood meal to the appropriate anatomical compartment.

We claim:

1. A composition comprising a compound having the formula:

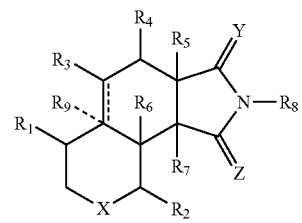

wherein
X is O, S, CR$_{10}$R$_{11}$, SiR$_{10}$R$_{11}$, or NR$_{10}$;
Y is O, S, CR$_{10}$R$_{11}$;
Z is O, S, CR$_{10}$R$_{11}$;
R$_1$-R$_{11}$ are each independently selected from the group consisting of hydrogen, hydroxyl, cyano, nitro, halogen, NH$_2$, SH, SR$_{12}$, OR$_{12}$, N(R$_{12}$)$_2$, OCON(R$_{12}$)$_2$, C(=O)R$_{12}$, OC(=O)R$_{12}$, C(=O)OR$_{12}$, COOH, COO$^-$M$^+$, CONH$_2$, CON(R$_{12}$)$_2$, C(=O)H, substituted or unsubstituted linear, branched, or cyclic alkyl, alkenyl, or alkynyl; substituted or unsubstituted linear, branched, or cyclic heteroalkyl, heteroalkenyl, or heteroalkynyl, substituted or unsubstituted aryl or heteroaryl, SOR$_{12}$, SOOR$_{12}$, SO$_3$R$_{12}$, SO$_4$R$_{12}$, NR$_{12}$COR$_{13}$, phosphoryl, sulfamoyl, and sulfonamido; wherein each occurrence of R$_{12}$ or R$_{13}$ is selected from the group consisting of hydrogen, substituted or unsubstituted linear, branched, or cyclic alkyl, alkenyl, or alkynyl; substituted or unsubstituted linear, branched, or cyclic heteroalkyl, heteroalkenyl, or heteroalkynyl, and substituted or unsubstituted aryl or heteroaryl;

wherein the dotted line represents a bond that is either present or absent; and wherein the compound is in an effective amount to inhibit digestion or nutrient processing in at least 40% of a population of blood-ingesting pests, reduce follicle size in female blood-ingesting pests compared to the follicle size when the pests are not exposed to the compound, or provide a lethal concentration against pest larvae, or a combination thereof, and wherein the compound is in a concentration of less than 0.25 mM.

2. The composition of claim 1, wherein the compound has the following stereochemistry

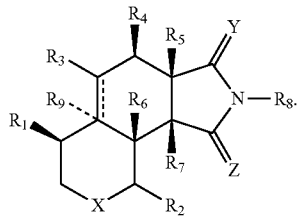

3. The composition of claim 1, wherein
X is sulfur;
Y is oxygen;
Z is oxygen; or
X is sulfur and Y and Z are both oxygen.

4. The composition of claim 1, wherein R$_1$ is a substituted or unsubstituted alkyl.

5. The compound of claim 4, wherein
R$_1$ is methyl;
R$_2$ is hydrogen;
R$_3$ is hydrogen;
R$_6$ is hydrogen;
R$_7$ is hydrogen; or
R$_4$ and R$_5$ are hydrogen.

6. The composition of claim 1, wherein R$_8$ is a substituted or unsubstituted aryl.

7. The composition of claim 6, wherein R$_8$ is a substituted or unsubstituted phenyl.

8. The composition of claim 7, wherein R$_8$ is an unsubstituted phenyl.

9. The composition of claim 1, wherein the compound is:

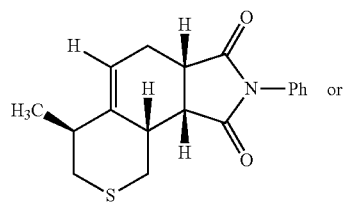

-continued

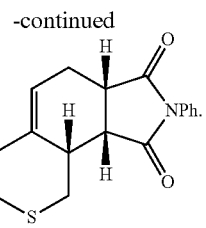

10. The composition of claim 1, wherein the compound has the formula:

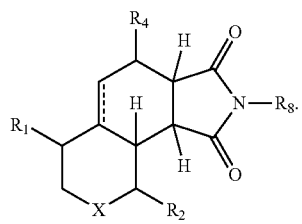

11. The composition of claim 1, in the form of a liquid is selected from the group consisting of a solution, suspension, dispersion, and an emulsion.

12. The composition of claim 1, wherein the effective amount of the compound is non-toxic to plants, animals, and/or arthropods that do not function as vectors of human pathogens.

13. A method of preventing the spread of mosquito-borne illnesses, comprising administering to a site or region containing one or more mosquitoes an effective amount of a composition comprising a compound having the formula:

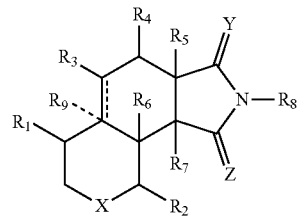

wherein
X is O, S, CR$_{10}$R$_{11}$, SiR$_{10}$R$_{11}$, or NR$_{10}$;
Y is O, S, CR$_{10}$R$_{11}$;
Z is O, S, CR$_{10}$R$_{11}$;
R$_1$-R$_{11}$ are each independently selected from the group consisting of hydrogen, hydroxyl, cyano, nitro, halogen, NH$_2$, SH, SR$_{12}$, OR$_{12}$, N(R$_{12}$)$_2$, OCON(R$_{12}$)$_2$, C(=O)R$_{12}$, OC(=O)R$_{12}$, C(=O)OR$_{12}$, COOH, COO$^-$M$^+$, CONH$_2$, CON(R$_{12}$)$_2$, C(=O)H, substituted or unsubstituted linear, branched, or cyclic alkyl, alkenyl, or alkynyl; substituted or unsubstituted linear, branched, or cyclic heteroalkyl, heteroalkenyl, or heteroalkynyl, substituted or unsubstituted aryl or heteroaryl, SOR$_{12}$, SOOR$_{12}$, SO$_3$R$_{12}$, SO$_4$R$_{12}$, NR$_{12}$COR$_{13}$, phosphoryl, sulfamoyl, and sulfonamido; wherein each occurrence of R$_{12}$ or R$_{13}$ is selected from the group consisting of hydrogen, substituted or unsubstituted linear, branched, or cyclic alkyl, alkenyl, or alkynyl; substituted or unsubstituted linear, branched, or cyclic heteroalkyl, heteroalkenyl, or heteroalkynyl, and substituted or unsubstituted aryl or heteroaryl;

wherein the dotted line represents a bond that is either present or absent; and wherein the compound is in an effective amount to inhibit digestion or nutrient processing in at least 40% of a population of blood-ingesting pests, reduce follicle size in female blood-ingesting pests compared to the follicle size when the pests are not exposed to the compound, or provide a lethal concentration against pest larvae, or a combination thereof, and wherein the compound is in a concentration of less than 0.25 mM.

14. The method of claim 13, wherein the site or region is a body of water or contains standing water.

15. The method of claim 13, wherein the compound is:

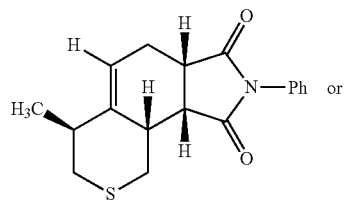 or

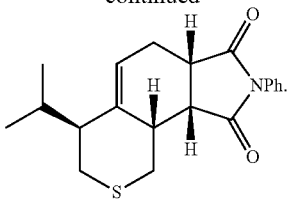

16. The composition of claim 1, wherein the composition formed by introducing pellets comprising the compound into a continuous aqueous phase.

17. The composition of claim 1, wherein the composition formed by introducing flakes comprising the compound into a continuous aqueous phase.

18. The composition of claim 1, wherein the composition is in the form of a liquid, and wherein the compound is dispersed or dissolved in an aqueous continuous phase.

19. The composition of claim 1, further comprising a wetting agent, surfactant, or carrier, or a combination thereof.

20. The compound of claim 19, wherein the composition comprises a surfactant, and wherein the surfactant is an anionic, cationic, amphoteric, or nonionic surface-active agent.

* * * * *